United States Patent
Park

(10) Patent No.: US 9,884,186 B2
(45) Date of Patent: Feb. 6, 2018

(54) APPARATUS FOR PHYSIOLOGICAL MECHANISM ACTIVATION AND THE METHOD COMPRISING THE SAME

(71) Applicant: Byongwon Park, Seoul (KR)

(72) Inventor: Byongwon Park, Seoul (KR)

( * ) Notice: Subject to any disclaimer, the term of this patent is extended or adjusted under 35 U.S.C. 154(b) by 825 days.

(21) Appl. No.: 14/359,651

(22) PCT Filed: Nov. 27, 2012

(86) PCT No.: PCT/KR2012/010085
§ 371 (c)(1),
(2) Date: May 21, 2014

(87) PCT Pub. No.: WO2013/122312
PCT Pub. Date: Aug. 22, 2013

(65) Prior Publication Data
US 2014/0330179 A1    Nov. 6, 2014

(30) Foreign Application Priority Data
Feb. 17, 2012 (KR) .................. 10-2012-0016596

(51) Int. Cl.
*A61N 1/36* (2006.01)
*A61B 5/01* (2006.01)
(Continued)

(52) U.S. Cl.
CPC .......... *A61N 1/36003* (2013.01); *A61B 5/015* (2013.01); *A61N 1/32* (2013.01);
(Continued)

(58) Field of Classification Search
CPC ............ A61N 1/36003; A61N 1/37247; A61N 5/0613; A61H 23/00; G06F 19/3406
(Continued)

(56) References Cited

U.S. PATENT DOCUMENTS

| 4,342,317 A | 8/1982 | Axelgaard |
| 2011/0288602 A1* | 11/2011 | Nachum ............ A61N 1/36014 607/3 |
| 2012/0109233 A1* | 5/2012 | Lee .................. A61F 7/007 607/3 |

FOREIGN PATENT DOCUMENTS

| JP | 2005-065812 A | 3/2005 |
| KR | 10-0779161 | 11/2007 |

(Continued)

OTHER PUBLICATIONS

International Search Report and Written Opinion dated Feb. 28, 2013, from the corresponding PCT/KR2012/010085.

*Primary Examiner* — Michael Carey
*Assistant Examiner* — Roland Dinga
(74) *Attorney, Agent, or Firm* — Novick, Kim & Lee, PLLC; Sang Ho Lee

(57) ABSTRACT

The present invention is related to an apparatus for activating electrophysiological mechanism and the method for configuring the same, which are based on diagnostic codes comprising at least more than two codes selected from a group of code classified by hue contrast to temperature differences according to heat distribution of a body. As a prescription for the above diagnostic codes, the activation prescription codes comprising code streams are generated, and then signals corresponding to each code are sequentially extracted and outputted as stimuli, and then finally become to provide activation stimuli to a body. The apparatus according to the present invention measures the distribution of body temperature, sets potential difference within an isolated system according to the distribution, and thus forces vibrations or waves with accelerated motion to be delivered to a whole body. Therefore, the present invention provides effects for being observed for electrophysiological mecha- (Continued)

nism, in which stimuli for physical treatment are delivered to a whole body as well as a special part of a body.

6 Claims, 3 Drawing Sheets

(51) Int. Cl.
  *A61N 1/372* (2006.01)
  *G06F 19/00* (2011.01)
  *A61N 1/32* (2006.01)
  A61N 5/06 (2006.01)
  A61H 23/02 (2006.01)
(52) U.S. Cl.
  CPC ..... *A61N 1/36021* (2013.01); *A61N 1/37247* (2013.01); *G06F 19/3406* (2013.01); *A61H 23/02* (2013.01); *A61N 5/06* (2013.01); *A61N 5/0613* (2013.01)
(58) Field of Classification Search
  USPC .................................. 607/76, 48, 88; 601/46
  See application file for complete search history.

(56) References Cited

FOREIGN PATENT DOCUMENTS

| | | |
|---|---|---|
| KR | 10-2009-0087229 A | 8/2009 |
| WO | 2010-035962 A2 | 4/2010 |

\* cited by examiner

US 9,884,186 B2

APPARATUS FOR PHYSIOLOGICAL MECHANISM ACTIVATION AND THE METHOD COMPRISING THE SAME

TECHNICAL FIELD

The present invention relates to an apparatus for activating electrophysiological mechanism and the method configuring the same, and in more details, it relates to the apparatus for being able to be used for the objectives of preventive health care, brain development and treatment of diseases through biological stimuli such as micro current, optics, wave, vibration, etc.

BACKGROUND

A variety of electromagnetic and physical stimulators for health cares or treatments of diseases have been developed. As an example, a micro current stimulator is an apparatus for applying low voltage pulses of less than 1,000 μA stimuli to a living body. This micro current is very much similar to the unique current being flowed in a living body, so the current is known to be effective to treat pain, inflammation, muscle contraction, wound healing, etc.

As another example, Korean patent No. 779,161 invented by the inventor and/or applicant of the present invention is an apparatus for providing the physiological mechanism activation. This apparatus is the device for providing multiple modes physiological mechanism activation, which increases the strength of stimulation and maximizes the treatment effects by providing both the sound waves and electrical stimulation modes based on sound and music, respectively.

Such conventional stimulation devices or apparatuses obviously provide a certain degree of effects. However, these kinds of simple one or two types of stimulation patterns cannot sufficiently reflect the stimulation transfer characteristic of a human body, so that the effects are limited to be very restrictive. On the other hand, the electrical stimulation signal flow is formed between two electrodes, and thus the stimulation is limited to be delivered across a whole body.

In short, according to the conventional devices, there are problems that the applied stimulation is not effective for treatment or management, and also is not effectively transferred to a whole body not by considering the current state of the body and using only a predetermined simple stimulation pattern; and in short it cannot control biological rhythms as a whole and is only applicable to local symptomatic treatment such as pain reduction, stiffness and sprain.

SUMMARY

The present invention is suggested for resolving problems stated in the previous conventional apparatuses. That is, the present invention is to provide an apparatus for activating electrophysiological mechanism and the method configuring the same, which can comprehensively activate electrophysiological mechanism by outputting treatment stimuli according to the suitable diagnosis and prescription by considering physical conditions in accordance with the distribution for a user's body temperature.

One objective in accordance with an embodiment of the present invention relates to an apparatus for activating electrophysiological mechanism, which is characterized by comprising; an input unit for inputting at least more than one diagnostic codes; a first processing unit for extracting activation prescription codes based on said diagnostic codes; a second processing unit for extracting the corresponding signals for said activation prescription codes; a central control unit for controlling the operations of the apparatus comprising said first processing unit and second processing unit; and a stimulus output unit for providing activation potential to body muscle by converting said corresponding signals to physical stimuli. Wherein said first processing unit and second processing unit can be merged into a single processing unit, which transforms said diagnostic codes into said activation prescription codes.

One objective in accordance with an embodiment of the present invention relates to the apparatus, wherein said input unit is capable of inputting said diagnostic codes via wired communication, wireless communication, or the combinations thereof through remote controlled devices.

One objective in accordance with an embodiment of the present invention relates to the apparatus, wherein codes comprising said diagnostic codes, prescription codes or the combinations thereof are 12 codes comprising number, letter, symbol, or the combinations thereof.

One objective in accordance with an embodiment of the present invention relates to the apparatus, wherein said stimuli are given in the type of current, light, or vibration, selectively or in combinations.

One objective in accordance with an embodiment of the present invention relates to the apparatus, wherein the activation prescription codes extracted by said first processing unit are stored and selectively used by switch.

One objective in accordance with an embodiment of the present invention relates to the apparatus, wherein group and rules defined in the electrophysiological mechanism activation prescription code table are used for selecting and extracting prescription codes according to the differences, which are read between normal code value and measured code value on a body temperature measurement device.

One objective in accordance with an embodiment of the present invention relates to the apparatus, wherein predefined code specific signal waveform and digital code as said each code specific signal are used for said each code specific signal.

One objective in accordance with an embodiment of the present invention relates to the apparatus, wherein as applying micro current stimulus to a body, the applied micro current is transferred to the whole body and maximizes the stimulus effects by using only a single electrode.

Another objective in accordance with an embodiment of the present invention relates to a method for configuring electrophysiological mechanism activation apparatus, which is characterized by comprising the steps of: a first step for receiving diagnostic codes; a second step for extracting activation prescription codes comprising a series of streams based on said received diagnostic codes; a third step for extracting the corresponding signals sequentially for said activation prescription codes; and a fourth step for providing activation potential to body muscle by converting said corresponding signals to physical stimuli. Wherein said second step and third step can be merged into a single step which extracts said activation prescription codes from said diagnostic codes.

Another objective in accordance with an embodiment of the present invention relates to the method, wherein the activation prescription codes in said second step can be repeatedly used by selecting switch, and said first step and second step can be substituted by the step for selecting specific activation prescription codes in the saving lists display.

Another objective in accordance with an embodiment of the present invention relates to the method, wherein said second step reads the difference between normal code value and measured code value on a diagnostic device, and select and extracts the prescription codes determined according to the difference.

BRIEF DESCRIPTION OF THE DRAWINGS

The accompanying drawings, which are included to provide a further understanding of the invention, illustrate the preferred embodiments of the invention, and together with the description, serve to explain the principles of the present invention. In drawings.

DETAILED DESCRIPTION

Hereinafter, the apparatus for activating electrophysiological mechanism and the method configuring the same in accordance with the present invention are described with reference to the accompanying drawings. Thus, the features and effects of the present invention, which are described above or not, will become more apparent through the embodiments, described hereinafter reference to the accompanying drawings.

Figure 1:
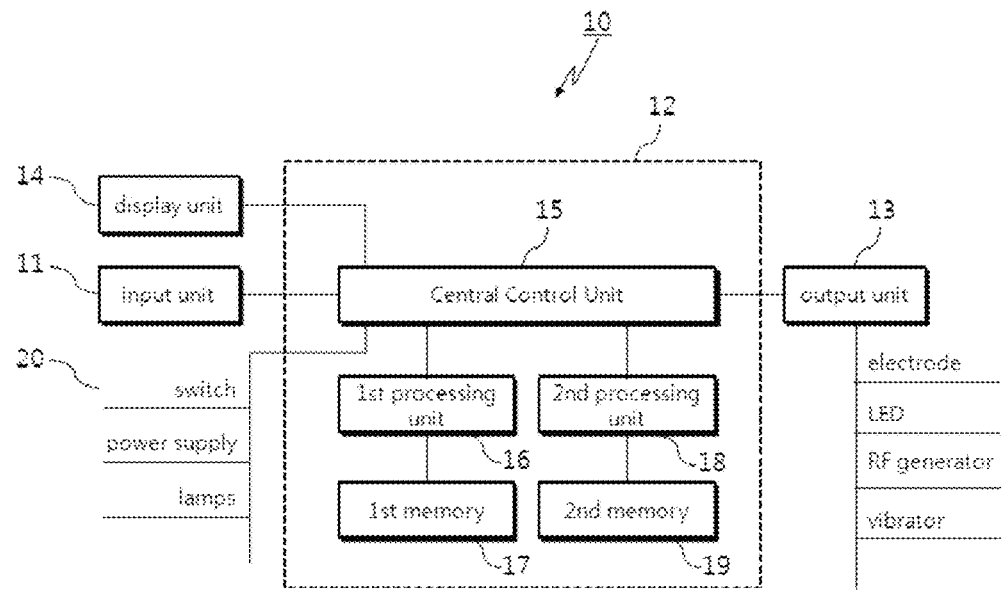
FIG. 1 shows a structure of an apparatus for providing electrophysiological mechanism activation in accordance with an embodiment of the present invention.

Referring to FIG. 1, reference numeral 10 denotes an apparatus for activating electrophysiological mechanism in accordance with the present invention. And said electrophysiological mechanism activation apparatus comprises a main unit (12) with a user input unit (11), a central control unit (15), and a stimulus output unit (13).

First, said user input unit (11) is a means for inputting diagnosis codes comprising more than two codes selected from a group of codes separated by temperature difference color contrast according to body temperature distribution of a body. In order to measure said body temperature distribution, conventional infrared thermo-graphic device can be utilized. However, no matter what the denomination classification of any device capable of measuring the body temperature and producing the colors can be used. This thermo-graphic device typically displays body temperature in the range of visible light separated into 12 different colors. Color gamut is, for example, depicted in FIG. 4.

Figure 4:
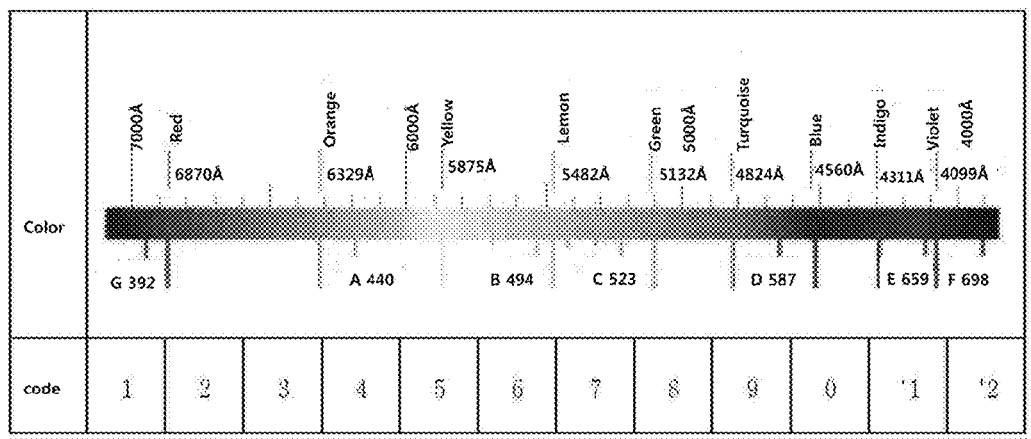
FIG. 4 shows a color gamut with each color having an assigned code.

As depicted in FIG. 4, a single code is assigned in each color. Therefore, the 12 codes including "1, 2, 3, 4, 5, 6, 7, 8, 9, 0, '1, '2" corresponding to the respective colors ranged from 'red' to 'violet' comprise a group of codes. These codes become keys for diagnosis and treatment suitable for the purpose of the usage of the apparatus for treatment, health management, etc.

As described above, said diagnostic codes are composed of two or more codes. However, said diagnostic codes are in fact usually composed of three or four codes stream, which is because of the fact that the result of measuring body temperature is generally described in three or four color bands.

In this embodiment of the present invention, said codes consist of numbers, but the codes can be described by including the forms of characters, symbols, and any other identifiable code.

In such a way, the diagnostic code is determined, and then the user inputs the diagnostic codes through wired, wireless or remote input unit (11). The 14 depicted in FIG. 1 is a display unit connected to the main unit (12), which is the means capable of identifying the operational processes of input device and other input peripheral units. While the usage of said input unit (11) and display unit (14) is for the major purpose of the input and output of diagnostic codes, respectively, these are possible to be used for general data input and output for the interactions with a user. Simply these can be implemented by using a touch screen device as well as a numeric keypad and a small liquid crystal display (LCD).

Next, said main unit (12) comprises a first processing unit (16), a second processing unit (18) and a central control unit (15).

Wherein, said first processing unit (16) performs the prescription in accordance with the diagnostic codes, and the prescription is performed by the method of extracting activation codes from a first memory (17), wherein the activation code comprises a series of code streams based on the inputted said diagnostic codes. In other words, a number of physiological mechanism activation codes for daily health management, brain development, disease treatment, etc. are stored in said first memory (17). And the diagnostic codes in accordance with the intended objectives of the usage for individual device or apparatus (10) are determined and inputted, then the appropriated activation prescription codes are thereby extracted from the individual device or apparatus (10).

As an easy example, for the case of a facial paralysis patient whose body thermal distribution is measured with facial center: red—bowl section: blue—extensive bone section: green by using infrared thermography diagnostic device and whose diagnostic code is determined to be "1-0-7", therefore he will be prescribed in principle to "2-1-4" direction or mode according to the principle of thermal equilibrium. More specifically, the prescription is determined by the electrophysiological mechanism activation code table considering energy transferability, accelerating ability, directivity, etc.

Table 1 illustratively shows an electrophysiological mechanism activation codes table used for extracting the appropriate activation prescription code based on the inputted said diagnostic code. This table is built with systemizing rules experimentally obtained by considering energy exchange, transition and activation between bands of said 12 codes. Accordingly, the activation prescription codes can be generated and extracted for each band and the whole system as the prescription for objectives of the usage and individual diagnostic code for a device or apparatus (10).

In practice, the activation codes are not regimentally generated and extracted such a method like a 1 group-1 rule-1 code arrangement. In Table 1, a plurality of rules can be applied in combination, and only a part of code arrangement can be applied for some rules. In this way, said first processing unit (16) extracts a series of code streams by using said 12 codes as activation prescription codes.

TABLE 2

Electrophysiological mechanism activation prescription codes table

| group | rules | activation prescription codes table |
|---|---|---|
| 1 | 1 | 182 23 304 45 5'26 67 728 89 940 0'1 '16'2 '21 |
|   | 2 | 1830 5'272 94'16 1830 5'272 94'16 1830 5'272 94'16 |
|   | 3 | 1836 5472 90'1'2 1836 5472 90'1'2 1830 5472 90'1'2 |
|   | 4 | 81 54 72 48 64 42 57 76 51 68 45 60 |
|   | 5 | 81 76 72 68 64 60 57 54 51 48 45 42 |
|   | 6 | 1'2 '26'1 '10 049 98 827 76 6'25 54 403 32 281 |
|   | 1-1 | '25'1 '10 039 98 817 76 6'15 54 493 32 271 1'2 |
|   | 2-1 | '2503 816'1 4927 '2503 816'1 4927 '2503 816'1 4927 |
|   | 3-1 | '2507 896'1 4321 '2507 896'1 4321 '2507 896'1 4321 |
|   | 4-1 | 5'2 89 6'1 95 79 9'1 86 67 8'2 75 98 73 |
|   | 5-1 | 5'2 67 6'1 75 79 73 86 89 8'2 95 98 9'1 |
|   | 6-1 | '21 172 23 394 45 5'16 67 718 89 930 6'1 '15'2 |
| 2 | 7 | 1: 1'2 18 14 10 13 17 |
|   |   | 2: 21 2'1 22 25 29 25 |
|   |   | 3: 34 30 33 37 3'2 38 |
|   |   | 4: 49 45 41 4'1 42 46 |
|   |   | 5: 57 5'2 58 54 50 53 |
|   |   | 6: 6'1 62 66 69 65 61 |
|   |   | 7: 70 73 77 7'2 78 74 |
|   |   | 8: 86 89 85 81 8'1 82 |
|   |   | 9: 93 97 9'2 98 94 90 |
|   |   | 0: 08 04 00 03 07 0'2 |
|   |   | '1: '16 '11 '1'1 '12 '16 '19 |
|   |   | '2: '22 '26 '29 '25 '21 '2'1 |
|   | 8 | 5: '2 4 7 0 4 '2 |
|   |   | 4: 5 0 '2 2 0 5 |
|   |   | 0: 4 2 5 7 2 4 |
|   |   | 2: 0 7 4 '2 7 0 |
|   |   | 7: 2 '2 0 5 '2 2 |
|   |   | '2: 7 5 2 4 5 7 |
|   | 9 | 8: 9 1 6 '1 1 9 |
|   |   | 1: 8 '1 9 3 '1 8 |
|   |   | '1: 1 3 8 6 3 1 |
|   |   | 3: '1 6 1 9 6 '1 |
|   |   | 6: 3 9 '1 8 9 3 |
|   |   | 9: 6 8 3 1 8 6 |

The activation codes prescribed as above can be stored according to necessity, and the switch (20) is used for selecting the stored specific activation prescription codes.

Said second processing unit (18) extracts corresponding signal according to the prescription performed in accordance with diagnostic codes. This extraction is performed by the method extracting sequentially signals corresponding to said activation codes from the second memory (19) storing signals set for each said 12 code, based on the activation prescription codes configured with code streams. That is, said second memory (19) stores signals corresponding to each code, and each corresponding signal is extracted sequentially by a series of streams for the delivered prescription codes.

Figure 5:
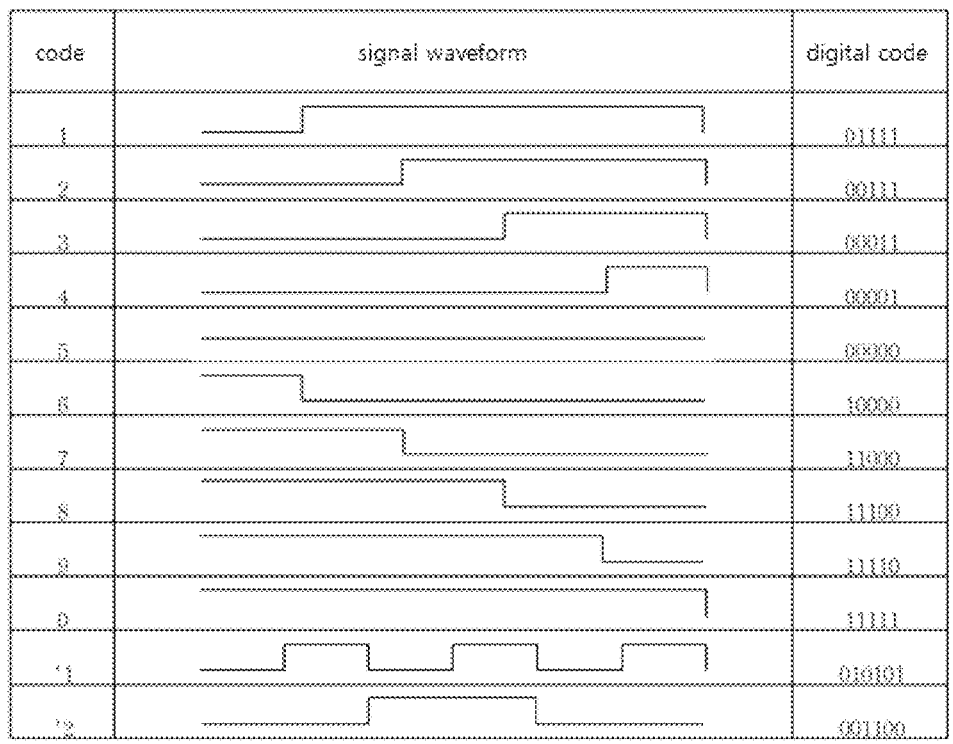
FIG. 5 shows a table for signal waveforms corresponding to each code.

FIG. 5 shows a table for signal waveforms corresponding to each code. This table is also built with systemizing optimal waveform for each band experimentally obtained by considering energy exchange, transition and activation between bands of said 12 codes. In the present invention, each corresponding signal waveform is continuously extracted in a sequence based on the prescribed activation codes, and each waveform can be designed to be variably applied to the signal output within 5-12 bits per a second.

Said central control unit (15) controls the whole operations of the device or apparatus (10). Importantly, the central control unit (15) performs the operations for the whole data processing and control of the first processing unit (16) and the second processing unit (18) in the device or apparatus (10), wherein the operations of the first processing unit (16) generates and stores activation prescription codes applying electrophysiological mechanism activation prescription code table stored in the first memory (17) based on the diagnostic codes inputted through the input unit (11), and those of the second processing unit (18) extracts and outputs corresponding signals referring to the electrophysiological mechanism activation prescription code table based on the generated of stored prescription codes.

And, said output unit (13) is a terminal means converting said corresponding signal to stimulus and providing activation potential to the body muscle. Preferably, said stimulus is micro current, but light, wave, or vibration can be applied selectively or in combination. This output unit (13) can comprise electrode, LED, RF generator, speaker, vibrator, and etc. for a specific configuration of the output unit.

The activation potential becomes to be applied to a body muscle by being attached to or in contact with the body, and the electrophysiological mechanism throughout the whole body becomes to be activated according to energy exchange and transition between bands. Wherein a single electrode is used for applying micro current stimulation to a body, and whereby the applied micro current is transmitted to the whole body and the stimulation effect can be maximized.

Figure 2:
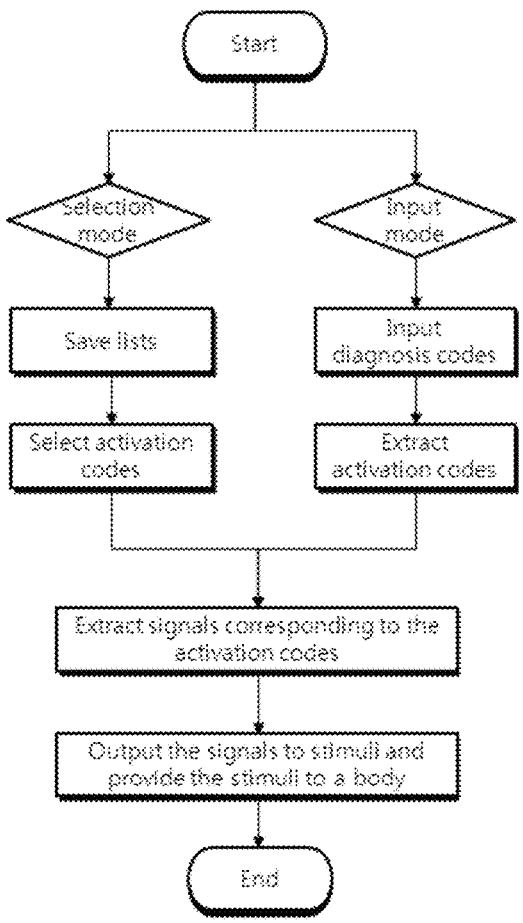
FIG. 2 shows an operational flowchart of an apparatus for providing electrophysiological mechanism activation in accordance with an embodiment of the present invention.

FIG. 2 shows an operational flowchart of an apparatus for providing electrophysiological mechanism activation in accordance with an embodiment of the present invention.

Referring to FIG. 2, the electrophysiological mechanism activation method based on the activation device or apparatus (10) is explained. First, at the same time when power is supplied to the activation device or apparatus (10), a user confirms the operations of the device or apparatus (10) through user interaction using the input unit (11) and the display unit (14). And the following steps are performed.

Step 1 (First Step)

Step 1 is the step for imputing diagnostic codes comprising more than 2 codes selected from a group of codes discriminated by color contrast for temperature difference according to the temperature distribution of a body. As described above, infrared body temperature diagnostic device is used, and said diagnostic codes are determined by the selected more than 2 codes because corresponding codes, 1, 2, 3, 4, 5, 6, 7, 8, 9, 0, '1 '2 are applied for each 12 color regions. The user becomes to input these diagnostic codes through the input unit (11).

Step 2 (Second Step)

Step 2 is the step for performing prescription for a diagnostic code of step 1. This step extracts and stores the activation prescription code comprising a series of code stream from the first memory (17). This step is performed with the method of extracting the activation prescription code comprising a series of code stream based on said diagnostic code inputted from said first processing unit (16). That is, said first memory (17) stores a plurality of electrophysiological mechanisms activation codes for performing daily health management, brain development, disease treatment, etc. And said diagnostic codes are determined and inputted according to the objectives of the usage for individual device or apparatus (10), and then the prescription codes appropriate for the diagnostic codes become to be extracted and stored. At this time, the electrophysiological mechanism activation code table is referred.

Above step 1 and step 2 are performed in "input mode". However, the activation codes stored in said step 2 can be used repeatedly by selecting switch (20). Therefore, said step 1 and step 2 in the "select mode" can be replaced with the step for selecting specific activation codes in the saving lists display.

Step 3 (Third Step)

Step 3 is the step for extracting sequentially each corresponding signals of said activation codes from the second memory (19) storing setting signals for each said codes. This step is carried out by the method of extracting sequentially each corresponding signal of said activation prescription code from the second memory (19), in which the second processing unit (18) stores individual setting signals for said 12 codes based on the activation prescription codes comprising code streams. At this time, signal waveforms table of FIG. 5 are referred.

Step 4 (Fourth Step)

Step 4 is the step for outputting stimulus for providing activation potential suitable to body muscles by converting said corresponding signals to current, light, wave or vibration. As described above, said output unit (13) is a terminal means for providing activation potential to body muscle by converting said corresponding signals to stimuli. Preferably, micro current may be used for said stimulus, light, wave or vibration is also applied for said stimulus selectively or in combination.

In the state that said output unit (13) is attached to or in contact with a body, stimuli generated throughout the above steps become to provide activation potential to a body muscle, and then electrophysiological mechanism over the whole body is activated according to the energy exchange and transition between bands. Activation codes as etiological cause or symptom analysis and the prescription for each color band, and digital codes corresponding to each color code are optimal results obtained experimentally for energy exchange, transition and activation between bands.

Figure 3:
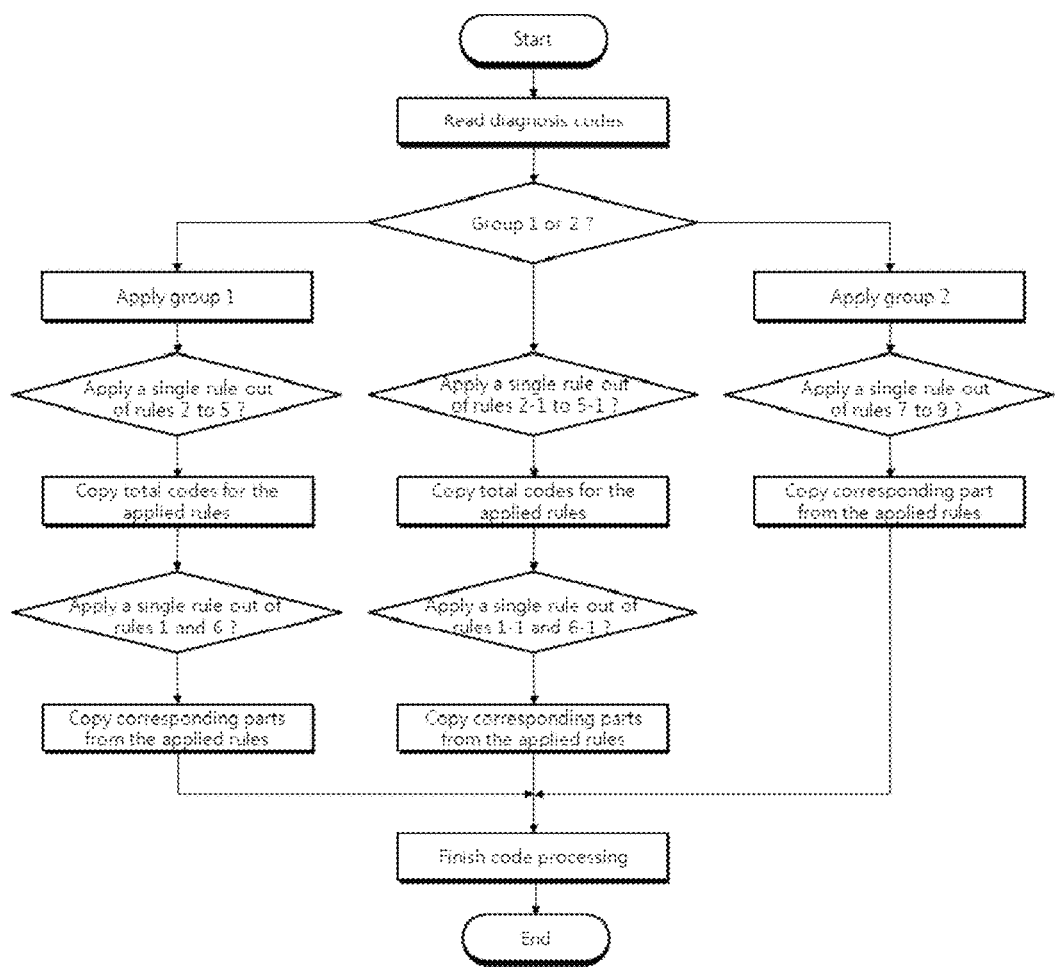
FIG. 3 shows a flowchart for generating treatment codes in the apparatus for providing electrophysiological mechanism activation in accordance with an embodiment of the present invention.

FIG. 3 shows a flowchart for generating treatment codes in the apparatus for providing electrophysiological mechanism activation in accordance with an embodiment of the present invention.

As shown in FIG. 3, the processes generate activation prescription codes referring to Table 1. Firstly, diagnostic codes are inputted, and the codes are read out and processed in the first processing unit (16) by applying group 1 or group 2 of Table 1. At this time, if the differences between normal code value and actual code value are less than 7, group 1 is selected, and contrary the difference are more than 7, group 2 is selected.

In fact, the former is the case that basic charge, that is, energy exists, and the latter, which is in many cases, is the case that locally no charge value exists. For example, if blue of '0' is measured at the portions of code 2 or 3 as normal value, then this portion is paralyzed or necrosis part, thereby this portion will be insufficient with normal group 1 prescription, and the prescription that especially forces to have basic charge at that portion is required at first.

Therefore, a special prescription is performed for this case in group 2. Of course, basic charge is generated at that portion so that group 1 will be able to be applied again. Other prescription codes can be applied for rules 7, 8 and 9 according to the degree of difference values among group 2. For example, code stream, 1, '2, 18, 14, 10, 13, 17 is prescribed as prescription codes for code 1 by applying rule 7.

Group 1 is separated into rules 1-6 and rules 1-1-6-1 having other prescription in accordance with the difference values. Firstly, rules 1-6 have the prescription codes of the method forcing thermal equilibrium to be in a whole body, and rules 1-1-6-1 have the prescription codes of the method forcing thermal equilibrium to be in a local body by forcing thermal equilibrium value to be given in a local body. Therefore, various prescription and stimulus can be provided according to the condition of a body and usage objectives of the device.

The prescription codes of said each rule become a series of prescription code by being extracted in a total or a part, and the corresponding signals are extracted sequentially and produces as stimuli, and then electrophysiological mechanism can be activated as a whole.

While the invention has been disclosed with respect to a limited number of embodiments and explained by referring to embodiments illustrated in accompanying drawings, a person skilled in the art, having the benefit of this disclosure, will comprehend numerous and equivalent modifications and variations therefrom. It is intended that the appended claims cover all such modifications and variations as fall within the true spirit and scope of the present invention.

What is claimed is:

1. A medical apparatus comprising:
   a display displaying colors representing measured temperatures of body parts, wherein each color represents a corresponding temperature range, and wherein each color is associated with a corresponding diagnostic code;
   a user input unit receiving at least two diagnostic codes from the user, the at least two diagnostic codes including: a first diagnostic code indicating a first temperature range of a first body part of a patient, and a second diagnostic code indicating a second temperature range of a second body part of the patient;
   a first processing unit retrieving, from a first memory, a first activation prescription code associated with the at least two diagnostic codes;
   the first memory comprising a non-transitory computer readable storage medium, and storing the first activation prescription code associated with the at least three diagnostic codes;
   a second processing unit retrieving, from a second memory, a first corresponding signal associated with the first activation prescription code;
   the second memory comprising a non-transitory computer readable storage medium, and storing the first corresponding signal associated with the first activation prescription code; and
   an output unit generating a stimulus output to a patient using the first corresponding signal, wherein the stimulus output is at least one of: an electrical signal to an electrode attached to the patient, an electrical signal to a light directed at the patient, an electrical signal to a radio-frequency generator directed to the patient, and an electrical signal to a mechanical vibrator mechanically attached to the patient,
   wherein the first activation prescription code is based, at least in part, upon differences between the received at least two diagnostic codes relative to respective normal values for the first and second body parts of the patient.

2. The medical apparatus of claim 1, wherein the first diagnostic code is associated with a center of a face, and the second diagnostic code is associated with at least one bone of the face.

3. The medical apparatus of claim 1, wherein the first memory includes a table associating activation prescription codes with diagnostic codes based upon energy exchange, transition, and activation.

4. A method for using a medical apparatus, the method comprising:

observing a display, wherein the display displays colors representing measured temperatures of body parts, wherein each color represents a corresponding temperature range, and wherein each color is associated with a corresponding diagnostic code;

inputting at least two diagnostic codes into a user input unit, wherein the user input device receives the least two diagnostic codes from the user, the at least two diagnostic codes including: a first diagnostic code indicating a first temperature range of a first body part of a patient, and a second diagnostic code indicating a second temperature range of a second body part of the patient;

retrieving, from a first memory, a first activation prescription code associated with the at least two diagnostic codes, wherein the first memory comprises a non-transitory computer readable storage medium, and stores the first activation prescription code associated with the at least two diagnostic codes;

retrieving, from a second memory, a first corresponding signal associated with the first activation prescription code, wherein the second memory comprises a non-transitory computer readable storage medium, and stores the first corresponding signal associated with the first activation prescription code; and generating a stimulus output to a patient based using the first corresponding signal, wherein the stimulus output is at least one of: an electrical signal to an electrode attached to the patient, an electrical signal to a light directed at the patient, an electrical signal to a radio-frequency generator directed to the patient, and an electrical signal to a mechanical vibrator mechanically attached to the patient, wherein the first activation prescription code is based, at least in part, upon differences between the received at least two diagnostic codes relative to respective normal values for the first and second body parts of the patient.

5. The method for using a medical apparatus of claim 4, wherein the first diagnostic code is associated with a center of a face, and the second diagnostic code is associated with at least one bone of the face.

6. The method for using a medical apparatus of claim 4, wherein the first memory includes a table associating activation prescription codes with diagnostic codes based upon energy exchange, transition, and activation.

* * * * *